United States Patent [19]
Lyddy, Jr. et al.

[11] Patent Number: 4,690,131
[45] Date of Patent: Sep. 1, 1987

[54] MEDICAL APPARATUS

[75] Inventors: James E. Lyddy, Jr., Arlington, Mass.; William Z. Penland; Paul H. Sugarbaker, both of Bethesda, Md.

[73] Assignee: The United States of America as represented by the Department of Health and Human Services, Washington, D.C.

[21] Appl. No.: 862,111

[22] Filed: May 12, 1986

Related U.S. Application Data

[63] Continuation of Ser. No. 740,171, May 31, 1985, abandoned.

[51] Int. Cl.⁴ .............................................. A61B 1/00
[52] U.S. Cl. ......................................................... 128/4
[58] Field of Search .................. 128/4, 6, 348.1, 325; 604/101

[56] References Cited

U.S. PATENT DOCUMENTS

| | | |
|---|---|---|
| 550,238 | 11/1895 | Allen, Jr. . |
| 2,687,131 | 8/1954 | Raiche ................. 128/349 |
| 2,767,705 | 10/1956 | Moore .................... 128/4 |
| 2,854,982 | 10/1958 | Pagano ................ 128/348 |
| 2,855,934 | 10/1958 | Daughaday, Jr. ........ 128/349 |
| 2,936,760 | 5/1960 | Gants .................. 128/349 |
| 3,045,677 | 7/1962 | Wallace ............... 128/349 |
| 3,050,066 | 8/1962 | Koehn ................. 128/349 |
| 3,144,868 | 8/1964 | Jascalevich ........... 128/350 |
| 3,631,848 | 1/1972 | Muller .............. 128/348 X |
| 3,882,852 | 5/1975 | Sinnreich ................ 128/4 |
| 3,895,637 | 7/1975 | Choy .................. 128/348 |
| 4,066,070 | 1/1978 | Utsugi ................... 128/4 |
| 4,148,307 | 4/1979 | Utsugi ................... 128/4 |
| 4,176,662 | 12/1979 | Frazer .................... 128/6 |
| 4,180,076 | 12/1979 | Betancourt ............ 604/101 |
| 4,198,981 | 4/1980 | Sinnreich .......... 604/101 X |
| 4,207,872 | 6/1980 | Meiri et al. ............... 128/4 |
| 4,224,929 | 9/1980 | Furihata ............. 128/6 X |
| 4,295,464 | 10/1981 | Shihata ............ 128/328 X |
| 4,404,971 | 9/1983 | Leveen et al. ....... 128/348.1 |
| 4,448,188 | 5/1984 | Loeb .................... 128/6 |
| 4,456,011 | 6/1984 | Warnecke ............ 128/325 |
| 4,577,621 | 3/1986 | Patel .................... 128/4 |

OTHER PUBLICATIONS

*NASA Technical Briefs*, Winter 1978, "Self-Propelling, Self-Locating Colonoscope", pp. 563–564, Frazer, Robert E.

*Colonoscopy, Diagnosis and Treatment of Colonic Diseases*, by Hiromi Shinya, Igaku-Shoin of New York City, N.Y. and Tokyo, Japan (1982) pp. 69–76 and 194.

*Primary Examiner*—William H. Grieb
*Attorney, Agent, or Firm*—Schiller, Pandiscio & Kusmer

[57] ABSTRACT

An improved device of a combination of elements is adapted to be used with an elongated flexible instrument, such as an endoscope, and capable of at least partially extending with the instrument into the lumen of a tubular body part, such as the large intestines. A sheath is adapted to be mounted on the instrument. The instrument and sheath are provided with selectively inflatable cuffs movable with respect to one another by axially sliding the sheath on the instrument. The movable relationship of the sheath and instrument and the selective control of air to the cuffs allows the user to more easily navigate the front of the instrument through the lumen of the body part with less discomfort to the patient.

29 Claims, 11 Drawing Figures

MEDICAL APPARATUS

PRIOR APPLICATION

This is a continuation of U.S. patent application Ser. No. 740,171, filed May 31, 1985 now abandoned.

The present invention relates generally to medical apparatus and, more particularly, to an improved apparatus for more easily and safely navigating a medical instrument, such as an endoscope, through the lumen of a tubular body part, such as the large intestines.

Generally, it is well-known to make instruments, designed to be inserted into a living tubular body part, such as the urethra, esophagus, stomach, small intestines, and large intestines, as an elongated flexible device so that the instrument can navigate through the lumen of the portion of the particular body part without perforating the walls of the particular body part through which the instrument passes. These flexible instruments have been known to include selectively inflatable elastic cuffs or balloons to position and/or navigate the instruments through a particular body part. For examples of such instruments see U.S. Pat. Nos. 550,238; 2,687,131; 2,854,982; 2,855,934; 2,936,760; 3,045,677; 3,050,066; 3,144,868; 3,631,848; 3,882,852; 3,895,637; 4,066,070; 4,148,307; 4,176,662; 4,180,076; 4,198,981; 4,224,929; 4,295,464; 4,404,971; 4,448,188; and 4,456,011. Also, see Frazer, Robert E.; "Self-Propelling, Self-Locating Colonoscope"; NASA's Jet Propulsion Laboratory, Pasadena, Calif.; NASA Tech Briefs, Winter 1978, pages 563 and 564. One such instrument is the flexible elongated endoscope, typically including fiber optics suitably encased in a cladding material, so as to form a fiber optic bundle. An objective lens is usually placed in front of the bundle. The fiber optic bundle and lens are fixedly secured within a elongated flexible sheath. See, for example, U.S. Pat. Nos. 4,066,070; 4,148,307; 4,176,662; 4,224,929 and the Frazer article. The flexible elongated endoscope is often used as an instrument for viewing, as well as conveying light and selected radiation (from a laser, for example), to the interior of the body part. The flexible fiber optic bundle and sheath are sufficiently flexible to allow navigation of the instrument through the lumen of the particular tubular body part.

Endoscopic instruments employing inflatable elastic cuffs are particularly useful in examining the large intestines since these instruments can be inserted through the anus and navigated through the intestines, against peristaltic action. The colonic endoscope must be carefully navigated through the large intestines in order to avoid perforating the colonic walls. This is usually accomplished by pushing the instrument up through the organ and twisting the instrument in order to turn the instrument around sharp turns, such as the hepatic flexure, where the ascending colon bends into the transverse colon, the splenic flexure where the transverse colon bends into the descending colon and the sigmoid flexure where the descending colon is convoluted before forming the rectum. In this way, the instrument can be used to examine the lumen of any part of the large intestines from the cecum to the rectum. The endoscopic instruments employing elastic inflatable cuffs are, therefore, made so that the sheathed instrument and the cuffs in their deflated state should be of a small diameter compared to that of the lumen of the large intestines to make the pushing and twisting of the instrument as easy as possible. Although the instruments are relatively flexible so that they can be twisted and turned around these portions of the large intestines, they, nevertheless, must be sufficiently stiff to be pushed forward. When the endoscopist wishes to observe and/or treat a particular location of the colon, the endoscopist inflates the cuff so that the cuff radially expands in all directions and grips the interior surfaces of the colon so as to hold the instrument in place. Air can then be pumped into the area of and expand the colon in order to improve the visibility of accessibility to the colonic walls.

Examples of such systems are shown, for example, in U.S Pat. No. 4,224,929, wherein two axially spaced inflatable cuffs are used to create a space so that forceps can be used to excise material from the colonic wall therebetween. U.S. Pat. Nos. 4,066,070; 4,148,307; 4,176,662 and the Frazer article suggest that the inflatable cuffs can also be used to help push the instrument through the lumen of the large intestine. Specifically, U.S. Pat. Nos. 4,066,070 and 4,148,307 each suggest an assembly of cuffs (two and three cuffs, respectively) for such use. Each assembly includes at least one deformable propelling cuff which is adapted to slide over at least one other cuff (while the latter is deflated) when the instrument is advanced. The deflated cuff can then be inflated and the propelling cuff deflated so that the latter cuff is forced back to its original position. In U.S. Pat. No. 4,176,662 and the Frazer article, a first inflatable annular cuff is fixedly secured to the sheath of the instrument. A second inflatable annular cuff, similar to the first cuff, is mounted on the sheath of the instrument behind the first cuff and axially slidable on the sheath toward and away from the front cuff. An expandable bellows is secured between and to both cuffs so that by selectively inflating the cuffs and bellows the instrument is pushed through the lumen of the large intestines. Specifically, with the front cuff deflated, the rear cuff is inflated so that it contacts and is securely held by the interior surfaces of the lumen. Air is transmitted into the bellows, causing the latter to expand so as to push the front cuff and thus the instrument forward. The front cuff can then be inflated and the rear cuff deflated. By withdrawing air from the bellows, the rear cuff is pulled toward the front cuff since it is free to slide on the external sheath of the instrument.

With all of the foregoing instruments, colonoscopy still is not performed routinely since pushing the instrument through the large intestines requires a great deal of skill so as not to perforate the intestine wall. Thus, total colonoscopy requires a highly trained physician for insertion, complete navigation of the endoscope and proper visual interpretation of the endoscopic findings. As a result, there are insufficient personnel to use colonoscopy to screen a large population. Further, large populations have not been routinely screened since it is not considered cost effective. It has become too expensive in terms of physician time and instrument cost, to offset the number of carcinomas found in the general population. Further, total colonoscopy as a screening tool is not known or accepted as necessary by the general public. Pushing the instrument through the large intestines can be extremely painful for a patient due to the inevitable stretching of the walls and mesentary of the large intestines. The inconvenience, discomfort and cost that a patient must experience during this examination may not be perceived as commensurate with the gains of large bowel cancer screening. As a consequence, even though evidence exists that total colonscopy can be extremely effective in screening the large bowel for polyps and cancer, such testing is not widely used in screening a large population.

Accordingly, a general object of the present invention is to reduce or overcome the above-noted problems of the prior art.

A more specific object of the present invention is to provide an improved device comprising a combination of elements adapted to be used with an elongated flexible instrument so that the instrument can be more easily navigated through the lumen of a tubular body part, such as the large intestine.

Another object of the present invention is to provide an improved device comprising a combination of elements adapted to be used with an elongated flexible endoscope so that the endoscope can more easily navigate the lumen of the large intestines.

And another object of the present invention is to provide an improved elongated flexible apparatus of the type including an endoscope and adapted to sequentially advance through the large intestines wherein a portion of the large intestines is gently straightened by pulling the intestines with the apparatus so that the endoscope can be advanced.

And yet another object of the present invention is to provide an improved colonoscopic endoscope for traversing the lumen of large intestines with less difficulty for the endoscopist, and less pain and discomfort for patients.

And still another object of the present invention is to provide an improved colonic endoscopic device which requires relatively less skill to use than current devices so as to encourage preventive colonoscopic screening of large populations.

Yet another object of the present invention is to provide an improved colonic endoscope for colonoscopic examinations and having greater patient acceptance.

Still another object of the present invention is to provide an improved colonic endoscopic device which will permit the relatively painless and rapid visualization of the entire lumen of the large bowel.

These and other objects of the present invention are achieved by an improved device capable of being used with an elongated flexible instrument of the type adapted to at least partially extend into the lumen of a tubular body part and having a front end for leading said instrument through said lumen and a rear end opposite said front end, said device comprising, in combination:

a front cuff adapted to be secured to said instrument in the proximity of said front end of said instrument and radially expandable so that said front cuff is capable of moving with said instrument through said lumen when said cuff is deflated, and contacting the interior walls of said body part when said front cuff is inflated;

an elongated flexible sheath capable of being coaxially mounted on and axially slidable with respect to said instrument between said front cuff and said rear end of said instrument so that said sheath is adapted to at least partially extend into said lumen with said instrument, said sheath comprising a forward end near and axially movable with respect to said front cuff and a back end near and axially movable with respect to said rear end of said instrument;

a rear cuff secured to said sheath in the proximity of said forward end of said sheath, said rear cuff being relatively movable with respect to said front cuff when said front cuff is secured to said instrument and said sheath is coaxially mounted on said instrument and radially expandable so that said rear cuff is capable of moving with said sheath through said lumen when said rear cuff is deflated, and contacting the interior walls of said body part when said rear cuff is inflated; and means for selectively inflating and deflating each of said front and rear cuffs;

wherein said sheath and rear cuff when mounted on said instrument are movable relative to said instrument and said rear cuff is inflatable so that at least a portion of said body part and the corresponding lumen can be straightened with said sheath and rear cuff and so that said instrument can advance through said corresponding lumen.

Other objects of the invention will in part be obvious and will in part appear hereinafter. The invention, accordingly, comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings, wherein.

In the drawings, the same numerals are used to refer to similar or identical parts.

Figure 1:
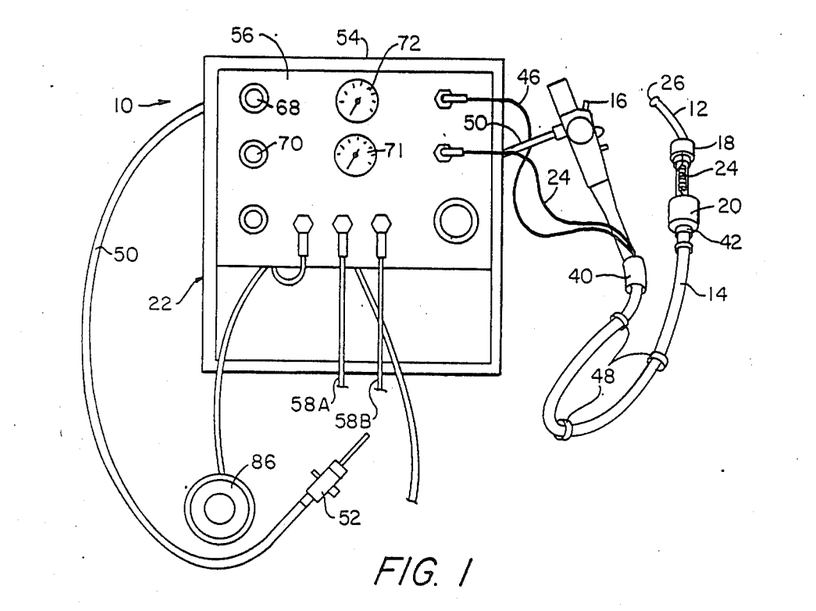
FIG. 1 is a top perspective view of the preferred embodiment of the apparatus of the present invention.

Referring to FIG. 1, the apparatus 10 includes an instrument 12, modified in accordance with the present invention. The instrument 12 is shown in the form of a colonic endoscopic instrument connected to a control section 16. In accordance with the present invention, the instrument is disposed within a flexible, axially movable sheath 14, and provided with the front cuff 18; while the sheath 14 is provided with the rear cuff 20. The rear cuff 20 is movable with respect to the front cuff 18, and selectively inflated and deflated by the control system 22, in order to straighten the colon so that the instrument can be more easily advanced through the colon, as will be more evident hereinafter.

The instrument 12 may be any type of elongated flexible instrument, such as a sigmoidoscope or colonoscope. For example, instrument 12 can be of a colonic endoscope of the type shown in U.S. Pat. Nos. 4,066,070 and 4,148,307, except that the front cuff 18, and associated pneumatic line 24, have been substituted for the various cuff assemblies and air supply lines used in the patented instruments. Although not illustrated in detail, such an instrument 12 can include flexible fiber optics suitably encased in a cladding material, so as to form a fiber optic bundle, an objective lens disposed at the forward end of the fiber optic bundle (for defining an image plane and/or an object plane depending on whether the fiber optic bundle is used for transmitting an image from or transmitting radiation to the front of the endoscope) at the front end 26 of the instrument 12. The fiber optic bundle and lens are fixedly secured within a elongated flexible sheath (separate and in addition to the sheath 14), typically made of a relatively soft elastomeric material, such as rubber or neoprene. The instrument 12 can include other devices, such as forceps, as shown in U.S. Pat. No. 4,224,929, and an air conduit for forcing air into the lumen under inspection in order to expand the walls of the colon to provide a better view of the walls.

Figure 2:
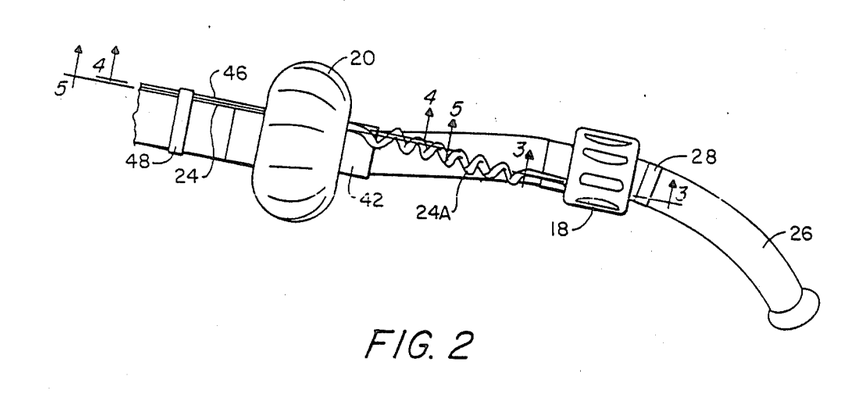
FIG. 2 is a side perspective view, partially cut away, of the front and forward ends of the sheath and instrument of the apparatus of FIG. 1.
Figure 3:
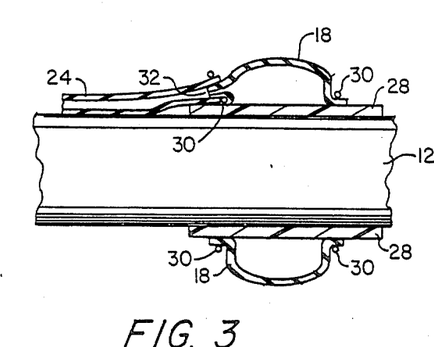
FIG. 3 is a cross-sectional view, partially cut away, taken along line 3—3 of FIG. 2.

The front cuff 18 is preferably made of an elastic material, such as a latex rubber, which will stretch when inflated and retain its original shape when deflated (cuff 18 being shown in the deflated condition in FIGS. 2 and 3). Front cuff 18 is circumferentially secured 360 degrees around the instrument 12 in the proximity of its front end 26. The front cuff is secured to the instrument in any suitable manner as, for example by a relatively rigid cylindrical sleeve 28, as best shown in FIGS. 2 and 3. The sleeve 28 is rigidly secured to the sheath of instrument 12 so that it will not move relative thereto. The cuff 18 has its forward and rearward annular edges secured to the sleeve 28 at axially spaced apart locations with any suitable means, such as annular sealing rings 30, so as to form the annular shape of the cuff and allow the cuff to uniformly expand in all radial directions when inflated. Each ring 30 seals the respective edge of the cuff to the sleeve to prevent air from leaking out from and fecal matter entering the inside of the cuff. The cuff 18 includes a narrowed opening 32 integrally formed as part of the cuff for allowing compressed air to enter the cuff when the latter is inflated, and withdraw air from the cuff when the cuff is deflated. Opening 32 of the cuff is suitably secured to the pneumatic line 24 to provide a tight seal therewith.

Figure 5:
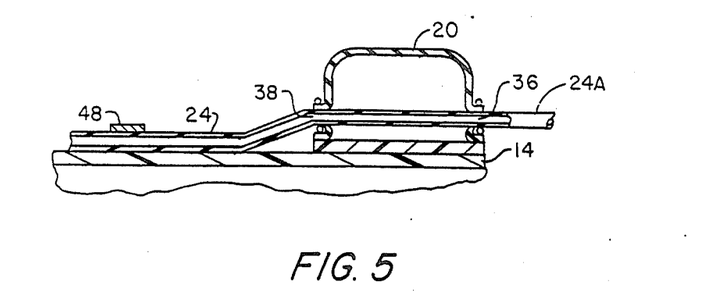
FIG. 5 is a cross-sectional fragmentary view taken along line 5—5 of FIG. 2.

The line 24 extends from the front cuff 18 to the rear cuff 20 where, as shown in FIG. 5, it extends through the rear cuff. Preferably, the portion of the line 24, indicated in FIG. 2 by the numeral 24A, between the cuffs 18 and 20 is made sufficiently elastic, and, for example, coiled so as to stretch and retract when the cuffs 18 and 20 are axially moved relative to one another. The coiling of portion 24A will, therefore, prevent slack in the line and interference of the line with the cuffs when the cuffs are positioned close to one another during the sequence described with respect to FIGS. 7A–7E, hereinafter.

The cuffs 18 and 20 are moved relative to one another in the direction of the elongated axis of the instrument 12 by use of the sheath 14. Sheath 14 is also made of a flexible material similar to the material of the sheath of instrument 12. For example, sheath 14 can be made of an elastomeric material such as rubber or neoprene, although it will be evident to those skilled in the art that other materials can be used. As will be evident hereinafter, both the sheath of the instrument and the sheath 14 can be made more flexible by, for example, making both of a softer elastomeric material than used for instrument sheaths of the prior art devices. Further, the outer diameters of the sheath of instrument 12 and sheath 14 can be such so as to be smaller than the outer diameters of the comparable prior art devices. The internal diameter of the sheath 14 is such that there is no radial movement of the sheath 14 relative to the instrument, yet the sheath easily slides axially along the instrument 12 so that the front end of the sheath 14 and, therefore, the rear cuff 20 moves relative to the front cuff 18. The length of the sheath 14 is such that the back end 40 of the sheath 14 is sufficiently axially spaced from the control unit 16 to allow for sufficient axial spacing between the two cuffs 18 and 20 when the latter are at their farthest spaced apart position. The sheath 14 includes a sleeve 42 formed or otherwise fixedly secured in the proximity of the forward end of sheath 14 for supporting the rear cuff 20. Sleeve 42 is sufficiently rigid to prevent the air pressure in the cuff 20, when the latter is inflated, from interfering with the components in the instrument passing axially through the cuff, as well as allowing the sheath 14 and instrument 12 to freely move relative to one another even when the cuff is inflated.

Figure 4:
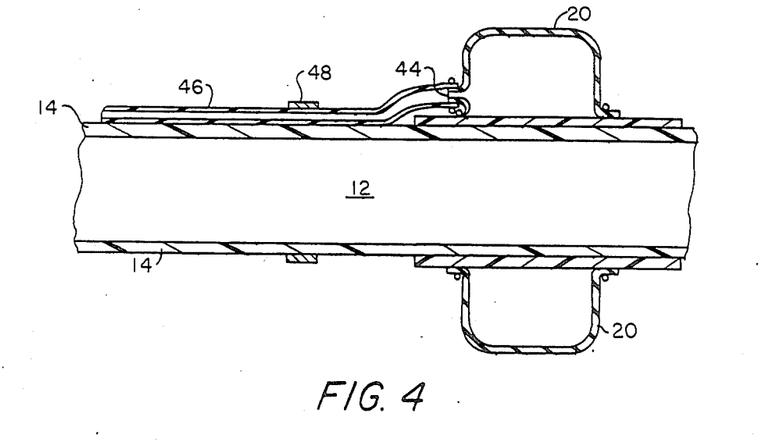
FIG. 4 is a cross-sectional view, partially cut away, taken along line 4—4 of FIG. 2.

The rear cuff 20, shown in detail in FIGS. 3 and 4, is made of the same material and is secured to the sleeve 42 in the proximity of the front end of the sheath in an essentially identical manner as the cuff 18 is secured to the sleeve 28 of the instrument 12. As shown in FIG. 4, the cuff 20 includes the opening 44 at its rear edge so that it can be secured in a suitable manner to a second pneumatic line 46 for transmitting air to the cuff 20 when the latter is inflated (shown inflated in FIGS. 2, 4 and 5) and for withdrawing air from the cuff when the latter is deflated.

The pneumatic lines 24 and 46 are suitably secured to sheath 14 along its outer surface (for example, with bands 48) so that the lines will not interfere with the navigation of the instrument and sheath through the large intestines when apparatus 10 is in use. The lines 24 and 46 extend from the back end 40 of the sheath 14 to the control system 22. Similarly, the lines for controlling the internal components of the instrument 12 extend from control unit 16 through cable 50, the latter being connected through the control system 22 to the connector 52 for connecting the instrument 12 to a source of power, light, radiation, analytical instruments, etc. for operating and using the instrument 12, as is well-known in the art.

Figure 6:
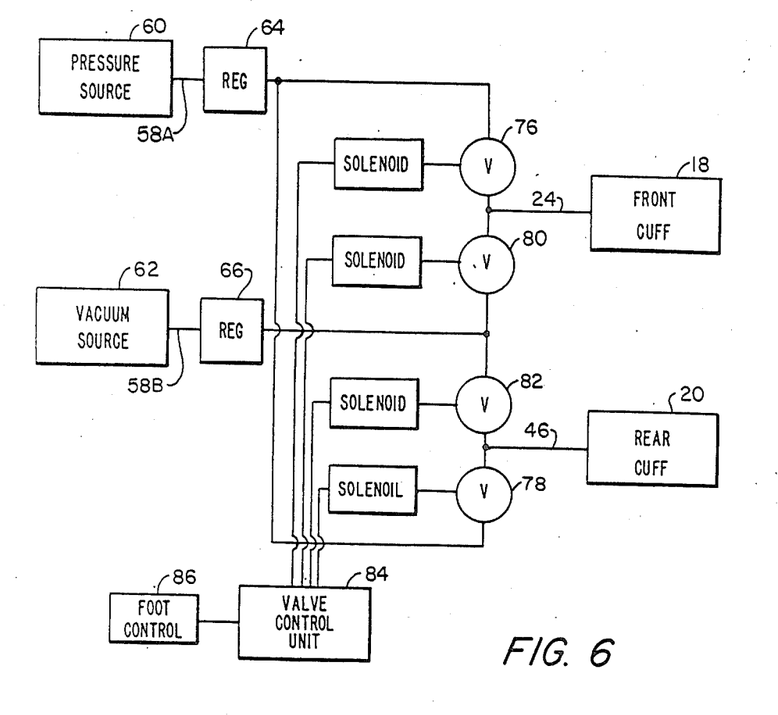
FIG. 6 is a block diagram of an example of a control system for controlling the pneumatic flow of air to and from the front and rear cuffs of the apparatus shown is FIGS. 1-5.

One embodiment of the control system 22 for selectively inflating and deflating the cuffs 18 and 20 will now be described with reference to FIGS. 1 and 6. More specifically, the control system 22 may be contained within a case 54 having a face plate 56 for supporting the various control knobs and dials for regulating the pressure of the air to and from the cuffs. The control system 22 is connected through pressurized line 58A to a source 60 (shown in FIG. 6) of compressed air of sufficient pressure to more than adequately inflate both cuffs 18 and 20. For example, source 60 can provide air at a pressure of 50 psi, although this can vary. Control system 22 is also connected through line 58B to a vacuum source 62 for deflating the cuffs. Lines 58A and 58B are connected through suitable pressure regulators 64 and 66, respectively (shown in FIG. 6). Regulators 64 and 66 can respectively include knob controls 68 and 70 and pressure dials 72 and 74 supported by the face plate 56 of the case 54, shown in FIG. 1. Referring to FIG. 6, the output of the regulator 64 is pneumatically connected to a pair of solenoid operated valves 76 and 78, while regulator 66 is pneumatically connected to a pair of solenoid operated valves 80 and 82. Valves 76 and 80 are pneumatically connected to line 24, which in turn, as previously described, is pneumatically connected to the front cuff 18. Similarly, valves 78 and 82 are pneumatically connected to line 46, which in turn is pneumatically connected to the rear cuff 20.

A valve control unit 84 controls the activation and deactivation of the solenoid operated valves 76, 78, 80 and 82 to selectively operate in one of three operator selected modes of operation, wherein a particular sequence can be repetitively carried out. The valve control unit 84 is not described in detail but may be an electro-mechanical system, for example, including a camming system having three sets of cams, one for each operating mode. One set of cams is rotatable through five operating positions with each revolution of the camming system for carrying out one mode, a second set of cams is rotatable through three operating positions with each revolution for the second operating mode, while the third set of cams is rotatable through two operating positions for the third operating mode. Each set of cams close the appropriate switches so as to energize the appropriate solenoids of the valves 76, 78, 80 and 82 at each operating position through a particular cycling sequence. Such a valve control unit 84 also includes a stepping motor coupled through a set of suitable gears associated with each set of cams for rotating the camming system to each operating position with each activation of the foot operating switch 86, which in turn energizes the stepping motor. As will be apparent hereinafter, the first set of cams and associated gears would carry out the sequence shown in FIGS. 7A-7E, the second set of cams and associated gears would carry out the sequence shown in FIGS. 7C-7E, while the third set of cams would maintain the rear cuff 20 deflated, while alternately inflate and deflate the front cuff 18. Suitable means, such as a set of linear actuators, can be used to axially move a common cam shaft supporting all three sets of cams so that a particular set of cams and gears can be selected for a particular mode of operation. The linear actuators can be actuated by an external mode selection switch (not shown). Alternatively, other control systems can be used, such as one including digital electronics for selectively activating each of the appropriate valves 76, 78, 80 and 82 with each activation of the switch 86 during the respective sequencing cycle.

Referring to FIGS. 7A-7E, the first mode of operation of the apparatus 10 will be described. The operator sets the mode of operation to provide the proper sequencing of the valve control unit 84 so that the sequence shown by FIGS. 7A-7E can be accomplished by successive activations of the foot switch 86. The operator of the apparatus 10 first activates the foot switch 86 a sufficient number of times to reach the first operating position shown in FIG. 7A wherein both valves 76 and 78 are closed (disconnecting the source 60 of pressurized air from the cuffs) and valves 80 and 82 are open (connecting the vacuum source 62 to the two cuffs). With both cuffs deflated the front end of the instrument 12 and sheath 14 can be inserted into the lumen of the tubular body part as, for example, through the anus into the large intestines. Preferably, the instrument 12 and sheath 14 are inserted into the intestines for a certain distance until a certain increased resistance is encountered.

Figure 7:
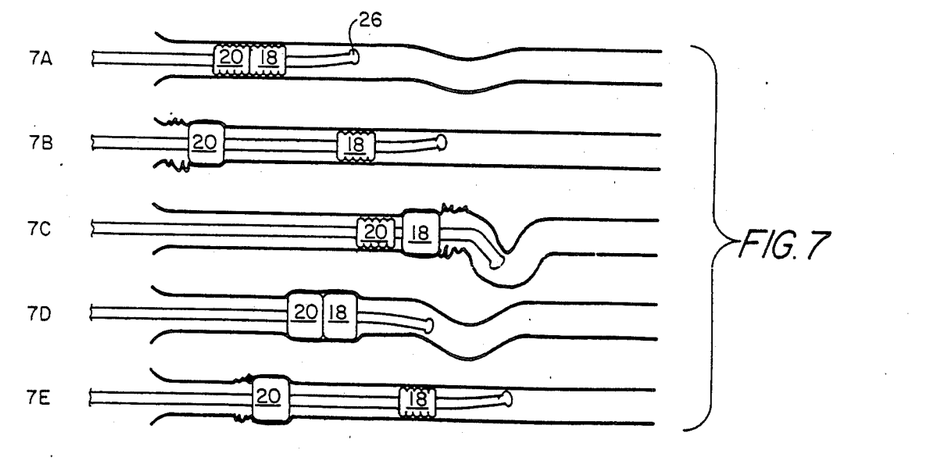
FIGS. 7A-7E are a sequence of simplified illustrations showing the use of the apparatus shown in FIGS. 1-6.

The foot switch 86 is then activated to advance the valve control unit 84 to the next operating position, wherein valve 80 remains open (maintaining the front cuff 18 deflated), and valve 82 is concurrently closed and valve 78 is open (so that the rear cuff 20 is now inflated). The inflated cuff 20 is expanded in all radial directions so as to grip the interior surfaces of the intestine wall. As shown in FIG. 7B, a gentle retrograde traction is placed on the sheath 14 by the operator at the back end 40 to pull the sheath axially backwards relative to the instrument 12. Pulling the intestine backward with the sheath 14 and inflated rear cuff 20 tends to have the simultaneous effect of tending to straighten the mucosal folds, as well as the general direction of the large intestines (as, for example, at the various flexures of the colon), at least a few centimeters, and advance the front end 26 of the instrument 12 with the deflated front cuff 18 in a forward direction through the colon. The front end 26 of the instrument 12 is then pushed forward further through the straightened colon advancing the instrument 12 with the front cuff 18 until resistance is encountered.

The next operating position, shown in FIG. 7C, is then performed by the activation of the foot switch 86. Specifically, valve 76 is open while the valve 80 is closed so as to inflate the front cuff 18, and with some delay the valve 82 is open and valve 78 is closed so as to deflate the rear cuff 20. The front cuff inflates sufficiently in all radial directions so as to grip the intestine walls so that when the rear cuff is subsequently deflated the apparatus will not slip backwards. The rear cuff can then deflate. With the rear cuff 20 now deflated the sheath 14 and cuff 20 can now be manually advanced by axially sliding th sheath 14 in a forward direction on the instrument 12. The sheath 14 is advanced until the sheath cannot be further advanced in a forward direction indicating the rear cuff 20 is adjacent the front cuff 18.

As shown in FIG. 7D, the next operating position accomplished by the activation of the foot switch 86 results in the valve 76 remaining open and valve 80 closed so that the front cuff 18 remains inflated, while the valve 82 is closed concurrently with the valve 78 being open so that the rear cuff 20 now becomes inflated. With both cuffs gripping the colon wall a gentle retrograde traction is provided by pulling both the sheath and instrument so as to straighten the colon at least a few centimeters.

As shown in FIG. 7E, the next operating position resulting from the activation of foot switch 86 results in valve 78 remaining open and valve 82 remaining closed, while valve 76 is now closed and valve 80 is open so as to apply a vacuum to the front cuff 18, causing the latter to deflate. The instrument 12 can now be advanced by pushing the instrument axially forward relative to the sheath 14 until resistance is encounted.

The apparatus has now reached the end of the operating cycle of the first operating mode. The next and each subsequent cycle can commence with the position shown in FIG. 7C and proceed through the positions shown in FIGS. 7D and 7E. Accordingly, the operator sets the apparatus for operation in the second operating mode for the proper sequencing of the valve control unit 84 to sequence the valves through the three positions.

The sequence of maneuvers is repeated in the second operating mode until the cecum is reached. As is well-known, when the cecum is entered, light transmitted through the abdominal wall appears at McBurney's point and characteristic anatomic features of this portion of the large bowel are recognized, e.g., the patulous lumen, the appendiced orifice and the ileocecal valve. Although orientation within a particular anatomic segment of the colon is maintained while advancing the instrument 12 and sheath 14 through the large intestines, careful visualization of the colon lumen preferably would be performed while the instrument 12 and sheath 14 is manually withdrawn by the user of the apparatus 10. In this instance, the valve control unit 84 is set to operate in the third mode of operation so as to maintain valve 78 closed and valve 82 open in order to maintain the rear cuff deflated through the sequenced cycle, while alternately opening valves 76 and 80 so as to alternately inflate and deflate the front cuff 18 with each activation of the foot switch 86. By alternately inflating and deflating the front cuff 18, the lumen opening can be expanded, facilitating the visualization of the colon wall during withdrawal of the instrument 12 and sheath 14.

The apparatus 10 thus is an improved medical apparatus for insertion in the lumen of a tubular body part, such as the large intestines. By using the slidable sheath 14 with the rear cuff 20 on an instrument 12 provided with cuff 18 and selectively inflating the cuffs as described, the instrument and sheath can more easily navigate through the lumen of a tubular body part, such as the large intestines. The instrument need only advance until resistance is met, eliminating the difficult twisting and pushing maneuvers necessary to force the prior art instruments, of the type described above, through the large intestines. Accordingly, the apparatus 10 provides an improved colonoscopic device for traversing the entire lumen of the large intestines permitting relatively painless and rapid visualization of the entire lumen of the large intestines with less difficulty for the user, and less pain and discomfort for the patient. It is hoped that by reducing patient pain and discomfort the apparatus 10 will have wider patient acceptance and encourage preventive colonoscopic screening of large populations.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A device capable of being used with an elongated flexible instrument of the type adapted to at least partially extend into the lumen of a tubular body part and having a front end for leading said instrument through said lumen and a rear end opposite said front end, said device comprising, in combination:

a front cuff adapted to be secured to said instrument in the proximity of said front end of said instrument and radially expandable so that said front cuff is capable of moving with said instrument through said lumen when said cuff is deflated, and contacting the interior walls of said body part when said front cuff is inflated;

an elongated flexible sheath capable of being coaxially mounted on and axially slidable with respect to said instrument between said front cuff and said rear end of said instrument so that said sheath is adapted to at least partially extend into said lumen with said instrument, said sheath comprising a forward end near and axially movable with respect to said front cuff and a back end near and axially movable with respect to said rear end of said instrument;

a rear cuff secured to said sheath in the proximity of said forward end of said sheath, said rear cuff being relatively movable with respect to said front cuff when said front cuff is secured to said instrument and said sheath is coaxially mounted on said instrument and radially expandable so that said rear cuff is capable of moving with said sheath through said lumen when said rear cuff is deflated, and contacting the interior walls of said body part when said rear cuff is inflated; and means for selectively inflating and deflating each of said front and rear cuffs;

wherein said sheath and rear cuff when mounted on said instrument are movable relative to said instrument and said rear cuff is inflatable so that at least a portion of said body part and the corresponding lumen can be straightened with said sheath and rear cuff and so that said instrument can advance through said corresponding lumen.

2. A device according to claim 1, wherein said means for selectively inflating and deflating each of said front and rear cuffs is adapted to deflate said front cuff so that said instrument is capable of moving in said lumen and adapted to inflate said rear cuff so that said rear cuff is forced into contact with said body part within said lumen, and said portion of said body part and the corresponding lumen are adapted to be straightened by applying a retrograde traction on said sheath.

3. A device according to claim 1, wherein said means for selectively inflating and deflating each of said front and rear cuffs inflates and deflates said cuffs cyclically in the following sequential steps:

(a) said rear cuff is inflated and retrograde pressure applied so that at least a portion of said body part and the corresponding lumen are straightened and said instrument can be subsequently advanced through said corresponding lumen;

(b) said front cuff is inflated and said rear cuff is deflated so that said sheath and rear cuff can be moved forward relative to said instrument and said front cuff; and (c) said front and rear cuffs are both inflated so that at least the next portion of said body part and the corresponding lumen can be straightened.

4. A device according to claim 1, further including means responsive to the operator of said device and instrument for operating said means for selectively inflating and deflating each of said cuffs through each step of said cycle.

5. A device according to claim 1, wherein said means for selectively inflating and deflating each of said front and rear cuffs maintains said rear cuff deflated and selectively alternately inflates and deflates said front cuff.

6. A device according to claim 1, wherein said means for selectively inflating and deflating each of said front and rear cuffs further includes means for selectively withdrawing the air from each of said front and rear cuffs so as to selectively deflate each of said cuffs.

7. A device according to claim 1, wherein said means for selectively inflating and deflating each of said front and rear cuffs comprises conduit means adapted to be secured to said device and apparatus for each of said cuffs for transmitting air to and from each of said cuffs.

8. A device according to claim 7, wherein said conduit means for transmitting air to and from said front cuff extends through said rear cuff.

9. A device according to claim 1, wherein said sheath includes an annular reinforced rigid section for supporting said rear cuff.

10. An apparatus comprising:

an elongated flexible instrument adapted to at least partially extend into the lumen of a tubular body part and having a front end for leading said instrument through said lumen and a rear end opposite said front end;

a front cuff secured to said instrument in the proximity of said front end of said instrument and radially expandable so that said front cuff is capable of moving with said instrument through said lumen when said cuff is deflated, and contacting the interior walls of said body part when said front cuff is inflated;

an elongated flexible sheath coaxially mounted on and axially slidable with respect to said instrument between said front cuff and said rear end of said instrument so that said sheath is adapted to at least partially extend into said lumen with said instrument, said sheath comprising a forward end near and axially movable with respect to said front cuff and a back end near and axially movable with respect to said rear end of said instrument;

a rear cuff secured to said sheath in the proximity of said forward end of said sheath, said rear cuff being relatively movable with respect to said front cuff and radially expandable so that said rear cuff is capable of moving with said sheath through said lumen when said rear cuff is deflated, and contacting the interior walls of said body part when said rear cuff is inflated; and means for selectively inflating and deflating each of said front and rear cuffs;

wherein said sheath and rear cuff are movable relative to said instrument, and said rear cuff is inflatable so that at least a portion of said body part and the corresponding lumen can be straightened with said sheath and rear cuff and so that said instrument can be led through said corresponding lumen.

11. An apparatus according to claim 10, wherein said means for selectively inflating and deflating each of said front and rear cuffs is adapted to deflate said front cuff so that said instrument is movable in said lumen and adapted to inflate said rear cuff so that said rear cuff is forced into contact with said body part within said lumen, and said portion of said body part and the corresponding lumen are adapted to be straightened by applying a retrograde traction on said sheath.

12. An apparatus according to claim 10, wherein said means for selectively inflating and deflating each of said front and rear cuffs inflates and deflates said cuffs cyclically in the following sequential steps:

(a) said rear cuff is inflated and retrograde traction applied so that at least a portion of said body part and the corresponding lumen are straightened and said instrument can be subsequently advanced through said corresponding lumen;

(b) said front cuff is inflated and said rear cuff is deflated so that said sheath and rear cuff can be moved forward relative to said instrument and said front cuff; and (c) said front and rear cuffs are both inflated so that at least the next portion of said body part and the corresponding lumen can be straightened.

13. An apparatus according to claim 10, further including means responsive to the operator of said apparatus for operating said means for selecting inflating and deflating each of said cuffs through each step of said cycle 14. An apparatus according to claim 10, wherein said means for selectively inflating and deflating each of said front and rear cuffs maintains said rear cuff deflated and selectively alternately inflates and deflates said front cuff.

15. An apparatus according to claim 10, wherein said means for selectively inflating and deflating each of said front and rear cuffs further includes means for selectively withdrawing the air from each of said front and rear cuffs so as to selectively deflate each of said cuffs.

16. An apparatus according to claim 10, wherein said means for selectively inflating and deflating each of said front and rear cuffs comprises conduit means secured to said apparatus for each of said cuffs for transmitting air to and from each of said cuffs.

17. An apparatus according to claim 16, wherein said conduit means for transmitting air to and from said front cuff extends through said rear cuff.

18. An apparatus according to claim 10, wherein said sheath includes an annular reinforced rigid section for supporting said rear cuff.

19. An apparatus according to claim 10, wherein said instrument is an endoscope, and the rear end of said endoscope is attachable to a system for operating said endoscope.

20. A device for facilitating the use of an instrument in at least a portion of the colon, said device comprising:

an elongated hollow tube sized so that at least a portion of said instrument is movable axially within said tube, said tube being adapted to be at least partially inserted into the colon; and gripping means secured to said tube and selectively retractable and extendable so that said gripping means is capable of (1) moving with the tube in the colon when said gripping means is retracted and (2) contacting and gripping the interior wall of said colon when said gripping means is extended so that said tube is relatively fixed with respect to the colon wall and said portion of said instrument can be moved axially within said tube so as to move said portion of said instrument relative to said portion of said colon.

21. A device according to claim 20, wherein said gripping means comprises a selectively deflatable and inflatable cuff, wherein said cuff is deflated when said tube is moved through the colon and inflated when said cuff grips the wall of the colon.

22. A device according to claim 21, wherein said cuff when inflated grips the interior wall of said colon sufficiently so that at least a portion of said colon can be at least partially straightened by applying a gentle retrograde traction on said tube.

23. A device according to claim 21, further including means for selectively (1) introducing air into said cuff so as to inflate said cuff and (2) withdrawing air from said cuff so as to deflate said cuff.

24. A device according to claim 21, wherein said cuff is secured to said tube in the proximity of the forward end of said tube which leads said tube through the colon when said tube is advanced through the colon.

25. A device according to claim 20, wherein said device includes second gripping means adapted to be secured to said instrument in the proximity of the front end of said instrument which leads said instrument and tube through the colon, said second gripping means being selectively retractable and extendable so that said second gripping means is capable of (1) moving with said instrument through the colon when said second gripping means is retracted and (2) contacting and gripping the interior wall of the colon when said second gripping means is extend so that said instrument is relatively fixed with respect to the colon wall.

26. A device according to claim 25, wherein said second gripping means comprises a selectively deflatable and inflatable cuff, when said cuff is deflated when said instrument is moved through the colon, and inflated when said cuff grips the wall of the colon.

27. A device according to claim 26, further including means for selectively (1) introducing air into said cuff so as to inflate said cuff and (2) withdrawing air from said cuff so as to deflate said cuff.

28. A method of facilitating the use of an instrument in at least a portion of the colon, said method comprising:
  inserting at least a portion of an elongated hollow tube into at least a portion of the colon;
  extending extendable gripping means secured to the tube so as to grip the interior wall of said poriton of the colon so as to fix the tube relative to said portion; and
  moving at least a portion of the instrument within and relative to said tube, so as to facilitate the use of said instrument in said portion of the colon.

29. A method according to claim 28, further including the step of applying a gentle retrograde traction on said tube when said gripping means is extended to grip the interior wall of said portion of said colon so that the portion of said colon is at least partially straightened.

* * * * *